United States Patent
Prosser et al.

(10) Patent No.: US 6,628,567 B1
(45) Date of Patent: Sep. 30, 2003

(54) SYSTEM FOR MULTIPLEXING ACOUSTIC EMISSION (AE) INSTRUMENTATION

(75) Inventors: William H. Prosser, Newport News, VA (US); Daniel F. Perey, Yorktown, VA (US); Michael R. Gorman, Englewood, CO (US); Edgar F. Scales, Chesapeake, VA (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 0 days.

(21) Appl. No.: 09/333,199

(22) Filed: Jun. 15, 1999

(51) Int. Cl.[7] .................... G01M 7/00; G01N 29/22; G01H 1/00
(52) U.S. Cl. .................. 367/13; 73/587; 73/594
(58) Field of Search .................. 73/587, 592, 594, 73/40.5 A; 367/13; 376/252, 258

(56) References Cited

U.S. PATENT DOCUMENTS

| | | | | | |
|---|---|---|---|---|---|
| 4,088,907 A | * | 5/1978 | Jones et al. | ................. | 310/333 |
| 4,609,994 A | * | 9/1986 | Bassim et al. | ................ | 73/587 |
| 5,117,676 A | * | 6/1992 | Chang | ..................... | 73/40.5 A |
| 5,255,565 A | * | 10/1993 | Judd et al. | .................... | 73/594 |
| 5,675,506 A | * | 10/1997 | Savic | ..................... | 73/40.5 A |

* cited by examiner

*Primary Examiner*—Ian J. Lobo
(74) *Attorney, Agent, or Firm*—Helen M. Galus

(57) ABSTRACT

An acoustic monitoring device has at least two acoustic sensors with a triggering mechanism and a multiplexing circuit. After the occurrence of a triggering event at a sensor, the multiplexing circuit allows a recording component to record acoustic emissions at adjacent sensors. The acoustic monitoring device is attached to a solid medium to detect the occurrence of damage.

23 Claims, 1 Drawing Sheet

SYSTEM FOR MULTIPLEXING ACOUSTIC EMISSION (AE) INSTRUMENTATION

ORIGIN OF THE INVENTION

The invention described herein was jointly made by employees of the United States government and employees during the performance of work under NASA Contracts NAS1-20582 and NAS1-20043. In accordance with 35 U.S.C. 202 the contractors elected not to retain title.

BACKGROUND OF THE INVENTION

1. Field of the Invention

The present invention relates to an acoustic monitoring device. More particularly, the acoustic monitoring device has a multiplexing circuit that records acoustic activity with the occurrence of a triggering event. Most particularly, the acoustic monitoring device may be used to detect, identify and assess damage within a solid medium.

2. Brief Description of the Related Art

Generally in acoustic emission (AE) monitoring, sensors remain active with each sensor having its own acquisition channel. As such, AE monitoring is extremely inefficient in monitoring acoustic emissions that occur at sporadic and random intervals and rates.

In a typical AE instrument, signals from each sensor are monitored by their own channel or data acquisition hardware, requiring the same number of channels of acquisition as acoustic sensors. In AE instruments which have fewer channels of data acquisition hardware than sensors, two approaches of switching sensors to data acquisition channels have been used. The first approach has been to assign certain sensors to be monitored. A manual or computer controlled switch is used to select which sensors are to be monitored. Unconnected sensors are not monitored during a given test, but can be connected for another test by disconnecting some of the previously monitored sensors. The second approach has been to switch sensors based on a clock or timing device. During a first period of time one group of sensors are connected to the data acquisition hardware and are actively monitored, while the remaining sensors are disconnected and ignored. At the end of this predefined first period of time, another group of sensors are connected by a switch and the original group disconnected. This method of data acquisition is widely used for monitoring a variety of sensor inputs such as temperature, pressure, strain, acceleration, ultrasonic sensors, etc.

The disadvantages of having one channel of data acquisition per sensor system are significant. These disadvantages include added weight, space, power, cost, etc. to an AE system. The acquisition hardware typically requires the most power and space, and is the heaviest part of an AE system. For aerospace applications, these additional weight and power requirements are unacceptable. Although conventional multiplexing reduces the number of data acquisition channels, a number of sensors are not actively monitored when they are disconnected from the data acquisition hardware. If a damage event occurs which generates an AE signal when the sensor is not being monitored, the damage event will not be detected.

Acoustic emission (AE) monitoring has been used for nondestructive evaluation in the petrochemical and power industries to monitor structures, such as pressure vessels. However, the use of large numbers of channels that are required for AE acquisition has limited AE monitoring for many applications. For example, AE monitoring for miles of piping in a typical petrochemical or nuclear power plant would require a large number of acoustic sensors. The complexity and expenses of the acoustic sensors and accompanying data acquisition hardware, per channel, restricts the ability to use AE monitoring. In other possible applications, such as structural monitoring for aircraft and spacecraft, the weight and power requirements for large numbers of data acquisition channels are limiting factors. In acoustic emission (AE) monitoring, a trade-off has existed between maximizing the number of AE sensors for accurate source location and signal detection, and the limitations (e.g., space, weight, cost, power, etc.) of the required instrumentation.

SUMMARY OF THE INVENTION

The present invention includes an acoustic monitoring device comprising the components of at least two acoustic sensors capable of sensing acoustic vibrations from a solid medium, a triggering mechanism responsive to a set parameter first occurring at one of the acoustic sensors, a multiplexing circuit connected to the triggering mechanism capable of receiving a triggering event and monitoring sensors adjacent to a triggered sensor, and at least one recording component responsive to the multiplexing circuit.

The present invention further includes a method for monitoring acoustic emissions comprising the steps of providing an acoustic monitoring device comprising the components of at least two acoustic sensors capable of sensing acoustic vibrations from a solid medium, a triggering mechanism responsive to a set parameter first occurring at one of the acoustic sensors, a multiplexing circuit connected to the triggering mechanism capable of receiving a triggering event and monitoring sensors adjacent to a triggered sensor, and at least one recording component responsive to the multiplexing circuit forming a connection between the acoustic monitoring device and the solid medium capable of detecting damage of the solid medium; and monitoring the sensors for a triggering event.

Additionally, the present invention includes an acoustic monitoring product made by the process comprising the steps of monitoring acoustic sensors for a triggering event within a solid medium and recording acoustical responses from at least one acoustic sensor after a triggering event occurs at an adjacent acoustic sensor.

The present invention is particularly applicable for detecting, locating and assessing damage to a solid medium, such as piping, aircraft, spacecraft, ships, buildings, and/or other similar structures, through the monitoring of acoustic vibrations within the solid medium.

DETAILED DESCRIPTION OF THE PREFERRED EMBODIMENT

Figure 1:
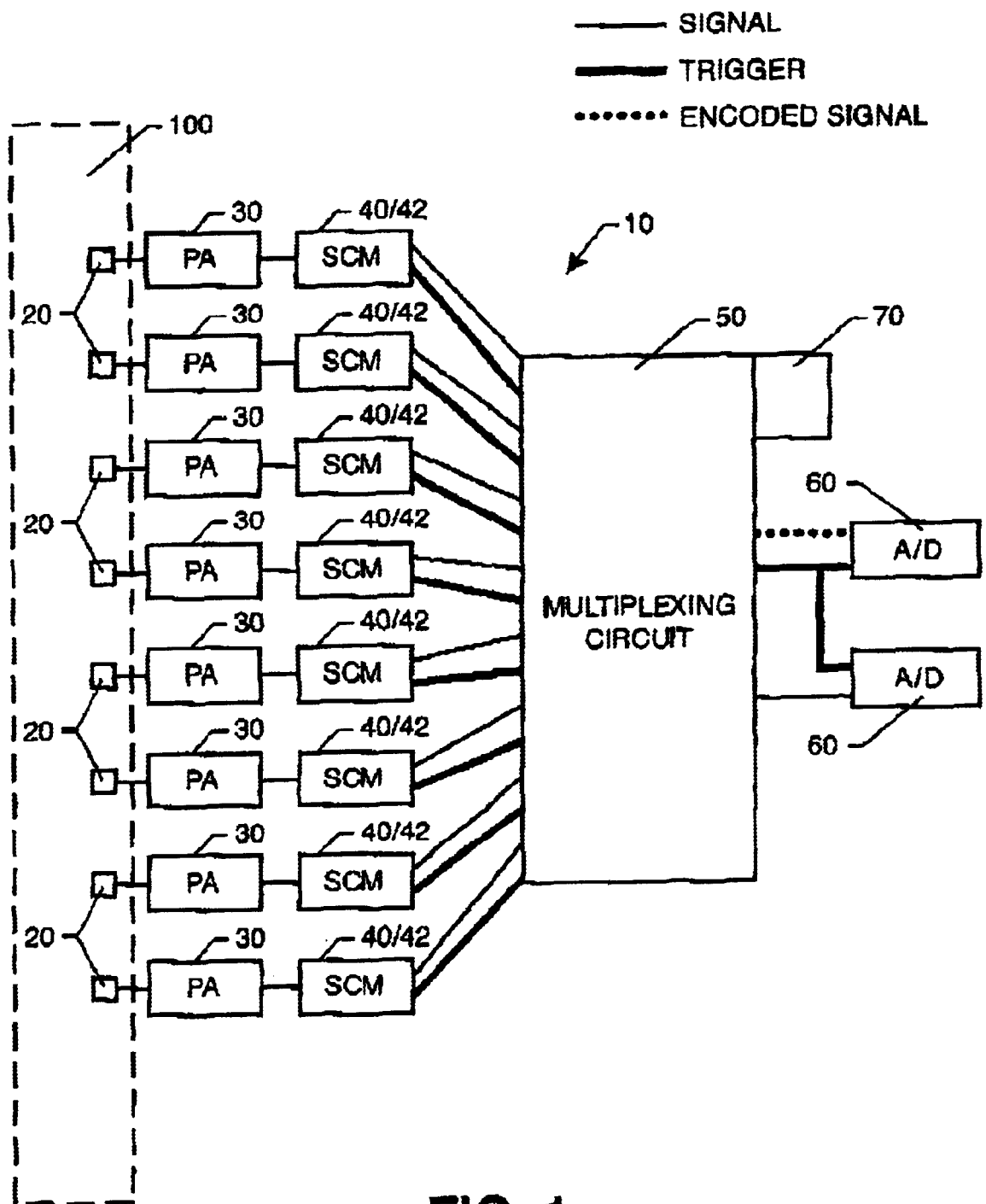
FIG. 1 shows a block diagram of a acoustic monitoring device of the present invention with eight acoustic emission sensors multiplexed into two data recording analog-to-digital hardware channels.

The present invention comprises a device, method and product useful in the monitoring of solid structures for detecting, locating and assessing damage to solid structures. The present invention multiplexes AE sensors into limited data acquisition hardware by switching system sensors in response to AE signals. The present invention is applicable to waveform digitizing AE systems, conventional parameter based AE systems which do not digitize the waveforms, and/or other parameter based multiplexing AE systems.

Damage for the purposes of the present invention includes any break, rupture, crushing, parting, splitting, failure, including catastrophic failure, and other like structural alterations of a solid medium that are generally unintended and/or unforeseen, but may include purposeful structural alteration of the solid medium, e.g., testing and evaluation of the solid medium. Damage includes cracks within oil pipes, splitting underwater hulls such as submarines, and nondestructive evaluation of air and space craft, such as the X-33 prototype space vehicle, Reusable Launch Vehicle (RLV), Space Shuttle, Space Station, civilian and military aircraft, and/or other solid structures subjected to internal and/or external forces.

The acoustic monitoring device of the present invention monitors the acoustic vibrations or signature of the solid structure in relation to set criteria, or predetermined triggering event, to activate a recording of possible alteration and/or damage occurring to the solid structure. The triggering event comprises an acoustic signal of a predetermined amplitude. Once the acoustic triggering event occurs at a sensor location, the acoustic monitoring device records the acoustic event at other sensor locations. By recording the acoustic event that caused the triggering of the acoustic monitoring device, the detected acoustic event reveals its origin, and the magnitude of the damage becomes assessable. By multiplexing the sensor to record the acoustic activity after the occurrence of a triggering event, a continuous monitoring of the solid medium occurs while conserving resources. This permits large area coverage.

As seen in FIG. 1, the acoustic monitoring device 10 of the present invention comprises acoustic emission (AE) sensors 20 connected to pre-amplifiers (PA) 30, signal conditioning modules (SCM) 40 that receive amplified AE noise from the pre-amplifiers 30, a multiplexing circuit 50, and recording devices 60.

The acoustic monitoring device 10 comprises at least two acoustic emission sensors 20. The AE sensors 20 of the present invention are connected to a solid medium 100 and are capable of sensing acoustic vibrations from the solid medium 100. As the AE sensors 20 receive acoustic emissions or vibrations from the solid medium 100, the vibrations are amplified by the pre-amplifiers 30 to a predetermined amount before passing to the SCM 40. As particular amplitude and/or frequency of the amplified vibrations for specific solid mediums 100 are likely to indicate damage to the solid medium 100, a triggering mechanism 42 within the SCM 40 is set to activate the acoustic monitoring device 10 with the occurrence of pre-selected vibrational amplitudes and/or frequencies. The triggering mechanism 42 remains dormant until the occurrence of the selected vibrational amplitudes and/or frequencies, and becomes responsive once the set parameters are met at one or more of the AE sensors 20. The set parameters constitute a "triggering event" of the acoustic monitoring device 10 at one AE sensor 20 that results in a recording of the triggering event at one or more adjacent AE sensors 20.

The acoustic emission sensors 20 may be integrally connected or temporarily attached to the solid medium 100. AE sensors 20 are integrally connected when the sensors 20 are formed within the solid medium 100, such as encapsulated into the solid medium 100 while the solid medium 100 is being formed, or attached in other ways that would require the destruction of or intrusion into the solid medium 100 to remove the acoustic sensors 20. Temporary attachment allows the acoustic sensors 20 to be repositioned, adjusted and/or moved in relation to the solid medium 100 without invading the physical integrity of the solid medium 100. Typically, the AE sensors 20 may comprise piezoelectric or other suitable contact compositions, and/or non-contact optically based or electromagnet acoustic transducers and the like.

The multiplexing circuit 50 receives an input from the triggering mechanism 42 that a triggering event has occurred. The multiplexing circuit 50 provides a switching mechanism that directs multiple channels into a more limited number of channels, with a control that determines which channels get switched. The multiplexing circuit 50 also provides information about which AE sensors 20 are being recorded. Within a waveform digitizing AE system, the latter portion of the conditioned signals is blanked out. A series of digital logic pulses, such as TTL, at a specific time relative to the trigger signal during the blanked out portion of the signal is used to encode which sensors 20 were recorded. The amount of blanking out time of the signal and encoding sensor identification is based on the number of points to be recorded, the digitization rate, and the amount of pre-trigger information to be recorded; with these parameters inputted to control the multiplexing system. With the receipt of a triggering event, the multiplexing circuit 50 initiates monitoring the AE sensors 20 that are adjacent to the triggered AE sensor 20. As the multiplexing circuit 50 monitors the adjacent AE sensors 20, the triggering event is recorded on at least one recording device 60. The pre-amplifiers 30 of the present invention include any amplifying component suitable for enhancing vibrations from the solid medium 100, with the type, size, capabilities and/or other characteristics of the pre-amplifiers being determinable by those skilled in the art. Examples of the pre-amplifiers 30 include the PA2040 G/A manufactured by Digital Wave Corporation of Englewood, Colo. Preferably the size of the pre-amplifiers 30 are small and light weight for ease of handling. The distance between the AE sensors 20 and the pre-amplifier 30 ranges in an amount sufficient to properly amplify the solid medium 100 vibrations, such as from about 4 feet or less.

The signal conditioning module 40 may be connected to the multiplexing circuit 50, or may be included within the multiplexing circuit 50. The SCM 40 may include elements to further amplify, attenuate, and/or filter the detected acoustic emissions. Generally, the SCM 40 comprises the triggering mechanism 42.

The acoustic monitoring device 10 includes at least one recording device or component 60 responsive to the multiplexing circuit 50. The number of recording devices 60 varies with the requirements of the acoustic monitoring device 10, with the number and type of recording devices 60 determinable by those skilled in the art. Exemplary recording devices 60 include the Fracture Wave Detector manufactured by Digital Wave Corporation of Englewood, Colorado. Preferably, the acoustic monitoring device 10 includes at least two recording devices 60 with analog-to-digital (A/D) hardware channels.

The components of the acoustic monitoring device 10 may transfer information by any means known in the art. Connections between the components include wires, fiber optics and/or radio transmitters/receivers at selected frequencies. The type of connection between different components may be varied in the same device, such as having wires between the acoustic emission sensors 20 and pre-amplifiers 30, fiber optics between the pre-amplifiers 30 and signal conditioning module 40, and radio communications between the signal conditioning module 40 and multiplexing circuit 50.

In operation, the present invention monitors acoustic emissions with the previously disclosed acoustic monitoring device 10. The acoustic monitoring device 10 is integrally or temporary attached to a solid medium 100 and is calibrated to operate at a given trigger parameter to detect the triggering event that generally indicates the occurrence of damage or alteration to the solid medium 100. Once the acoustic monitoring device 10 is attached and set, the AE sensors 20 monitor for the triggering event.

With the occurrence of an acoustic vibration within the solid medium 100 that raises to the level of a triggering event, the acoustic monitoring device 10 is activated. The acoustic emission sensor 20,closest to the origin of the acoustic vibrations transmits an electrical signal to the corresponding SCM 40. The SCM 40 then transmits a trigger to the multiplexing circuit 50. Using this trigger, the multiplexing circuit 50 rapidly switches to allow the conditioned signals from the neighboring AE sensors 20 to be passed to the data acquisition channels into the recording devices 60. As the acoustic event arrives at the neighboring AE sensors 20, the acoustic vibrations are fully recorded.

The signals from the neighboring AE sensors 20 are used to record the acoustic event, instead of the initially triggered AE sensor 20, to allow capture of the full waveforms of the acoustic vibrations. Acoustic vibrations may occur at the beginning of the triggering event and remain non-triggering because of a small amplitude until a sufficiently large acoustic vibration appears to create the triggering event. However, the small amplitude vibrations at the front end of the triggering event provide accurate source location information for determining the initial position of the acoustic vibration generation. Any recording of the triggering AE sensor 20 would not capture acoustic vibrations occurring before the arrival of the triggering event at that AE sensor 20. With the time delay of acoustic signal propagation through the solid medium 100, capture of the complete acoustic event becomes possible at the neighboring acoustic emission sensors 20 and full waveforms are captured for analysis. The acoustic emissions are recorded from at least one adjacent AE sensor 20 to a monitored AE sensor 20 registering a triggering event, and preferably are recorded from at least two adjacent AE sensors 20 to a monitored AE sensor 20 registering a triggering event.

Different solid structures or medium 100 provide different acoustic signal propagation speeds. The solid medium 100 may include singular compositions, or combinations of solid structures, such as metal alloys, metal composites, welded, adhered, bonded, coupled and/or other unified solid structures that may transmit acoustical emissions therethrough. Generally, the vibrational triggering event within the solid medium 100 remains inaudible to human hearing.

The number of AE sensors 20 required to detect damage and/or determine the location of the origin of the triggering event varies with the type of solid medium 100 being analyzed. Within a linear array, particular useful in pipelines, a first "triggering" AE sensor 20 together with at least one other "recording" sensor 20 are needed to detect and record damage to the solid medium 100, with at least one additional AE sensor 20 required to determine the location of the triggering event. With three AE sensors 20 to monitor a pipeline, the two nearest neighbor AE sensors 20 to the triggered AE sensor 20 are monitored to provide linear location information. As such, at least three AE sensors 20 are used within linear array, with four AE sensors 20 required for locating the triggering event within planar arrays, useful in storage tanks or other similar objects. Five AE sensors 20 are needed in spatial arrays. With the proper number of AE sensors 20, the acoustic monitoring device 10 identifies the source, or location, of the damage.

Analysis of the acoustic event is performed by software 70 to detect and decode the logic pulses and properly locate the AE source relative to the correct AE sensors 20 in the sensor array. The magnitude of the detected and located damage may be assessed within the solid medium 100. With the recording of the full waveform of the triggering event, analysis allows calculation of the type and degree of damage to the solid medium 100.

The arrangement of the AE sensors 20 and the type and method of recordation of the acoustic vibrations provides an acoustic monitoring product that may be analyzed to assess damage to the solid medium 100. The acoustic monitoring product results from the monitoring of the acoustic emission sensors 20 for a triggering event within the solid medium 100 and recording acoustical responses from AE sensors 20 after a triggering event occurs at adjacent AE sensors 20. The acoustic emission monitoring product may be in the form of graphic or plotted depictions, mathematically tabulated values, computerized data, and/or any other recording suitable for retaining acoustic emission information.

Example 1

A linear arrayed multiplexing AE system with eight AE sensor channels was multiplexed into two data acquisition channels (8:2 multiplexing ratio). Each sensor channel had its own pre-amplifier and SCM. Each SCM provided a conditioned signal output and independent trigger signal. The solid medium was a graphite/epoxy composite tube and pencil lead breaks were used to simulate AE signals or acoustic events at different locations along the tube. The sensors, pre-amplifiers, SCM and A/D were constructed from a Digital Wave Corporation Fracture Wave Detector (FWD) system, manufactured by Digital Wave Corporation of Englewood, Colo., with the conditioned signal and trigger from the SCM taken from internal connections within the FWD system and routed by coaxial cables to the multiplexing circuit. The output of the multiplexing circuit was routed by coaxial cable back to the internal input of the AID modules of the FWD system. Analysis of the signal provided the location of the acoustic event within the linear array, and showed the acoustic events that occurred outside of the linear array. With the sensors numbered 1 through 8, with 1 and 8 at the end points of the linear array, multiplexing switching occurred as follows:

| Trigger Sensor | Sensor Signals Sent to Acquisition Hardware |
|---|---|
| 1 | 1 and 2 |
| 2 | 1 and 3 |
| 3 | 2 and 4 |
| 4 | 3 and 5 |
| 5 | 4 and 6 |
| 6 | 5 and 7 |
| 7 | 6 and 8 |
| 8 | 7 and 8 |

The following specifications were used:

Conditioned AE signals from the SCM that were inputted into the multiplexing circuit had a maximum 10 volts P-P with approximately 5 millivolts P-P noise. Conditioned AE signal bandwidth was between about 0.01 and 2.0 MHz. Multiplexing switching time occurred within 1 microsecond of the trigger, with added vibrations and transients from the switching being less than about 5 millivolts P-P. The original trigger signal from the passed through the multiplexing circuit 50 to the recording device 60.

Example 2

AE sensors are temporary attached in a linear array along an oil pipe. The AE sensors are attached to pre-amplifiers that connect to signal conditioning modules tied to a multiplexing circuit. As areas of the pipe begin to fail, vibrations in the form of acoustic emissions are collected by the AE sensors and amplified by the pre-amplifiers. When the acoustic emissions reach a level to cause a triggering event, the SCM relays the trigger signal to the multiplexing circuit. The multiplexing circuit rapidly switches to allow the conditioned signals from the neighboring AE sensors to be passed to the data acquisition channels. The acoustic emissions are collected from the adjacent AE sensors and recorded to determine the location and magnitude of the failing areas of the pipe.

Example 3

AE sensors are permanently molded into a ship hull in a planar array. The AE sensors are attached to pre-amplifiers that connect to signal conditioning modules tied to a multiplexing circuit. As the ship hull experiences forces, the acoustic emissions are collected by the AE sensors and amplified by the pre-amplifiers. When the acoustic emissions reach a level to cause a triggering event at one of the AE sensors, the SCM relays the trigger signal to the multiplexing circuit. The multiplexing circuit rapidly switches to allow the conditioned signals from the neighboring AE sensors to be passed to the data acquisition channels. The acoustic emissions collected from adjacent AE sensors next to the triggered AE sensor are recorded to determine the location of the triggering event, and assess the likelihood of ship hull failure.

Example 4

AE sensors are permanently molded into a spatial array within a solid propellent in a space shuttle. The AE sensors are attached to pre-amplifiers that connect to signal conditioning modules tied to a multiplexing circuit. Vibrations are monitored by the AE sensors and amplified by the pre-amplifiers. When the acoustic emissions reach a level to cause a triggering event at one of the AE sensors, the SCM relays the trigger signal to the multiplexing circuit. The multiplexing circuit rapidly switches to allow the conditioned signals from the neighboring AE sensors to be passed to the data acquisition channels. The acoustic emissions collected from adjacent AE sensors next to the triggered AE sensor are recorded to determine the location of the triggering event, and assess the likelihood of damage to the propellent. With the occurrence of particular triggering events, the propellent is automatically jettisoned from the space shuttle.

Example 5

AE sensors are attached to several first solid mediums that are bound to a second solid medium. The AE sensors are attached to pre-amplifiers that connect to signal conditioning modules tied to a multiplexing circuit. As faults are formed in the second solid medium, acoustic emissions travel into and through the first solid medium from the second solid medium and are monitored by the AE sensors attached to the first solid medium. When the acoustic emissions reach a level to cause a triggering event at one of the AE sensors on the first solid medium, the SCM relays the trigger signal to the multiplexing circuit. The multiplexing circuit rapidly switches to allow the conditioned signals from neighboring AE sensors to be passed to the data acquisition channels. The acoustic emissions collected from the adjacent AE sensors are recorded to determine the location of the triggering event, and assess the likelihood of failure in the second solid medium.

The foregoing summary, description, examples and drawing of the present invention are not intended to be limiting, but are only exemplary of the inventive features which are defined in the claims.

What is claimed is:

1. An acoustic monitoring device, comprising the components of:
   at least two acoustic sensors capable of sensing acoustic vibrations from a solid medium;
   a triggering mechanism responsive to a set parameter first occurring at one of the acoustic sensors;
   a multiplexing circuit connected to the triggering mechanism and configured to receive a triggering event and in response thereto select and monitor sensors adjacent to a triggered sensor; and
   at least one recording component configured to record acoustical responses from at least one of said at least two acoustic sensors, the at least one recording component being responsive to the multiplexing circuit.

2. The acoustic monitoring device of claim 1, further comprising a pre-amplifier connected to the sensors.

3. The acoustic monitoring device of claim 2, wherein the distance between the sensors and the pre-amplifier ranges from about 4 feet or less.

4. The acoustic monitoring device of claim 1, further comprising a signal conditioning module connected to the multiplexing circuit.

5. The acoustic monitoring device of claim 4 wherein the signal conditioning module comprises the triggering mechanism.

6. The acoustic monitoring device of claim 5, wherein the multiplexing circuit comprises the signal conditioning module.

7. The acoustic monitoring device of claim 1, comprising at least two recording components.

8. The acoustic monitoring device of claim 1, wherein the components communicate therebetween by a connection selected from the group consisting of wire, fiber optics, radio frequency and combinations thereof.

9. The acoustic monitoring device of claim 1, wherein the solid medium is present and integrally connected to the acoustic sensors.

10. The acoustic monitoring device of claim 1, wherein the solid medium is present and temporarily attached to the acoustic sensors.

11. A method for monitoring acoustic emissions, comprising the steps of:
   providing an acoustic monitoring device comprising the components of at least two acoustic sensors capable of sensing acoustic vibrations from a solid medium, a triggering mechanism responsive to a set parameter first occurring at one of the acoustic sensors, a multiplexing circuit connected to the triggering mechanism and configured to receive a triggering event and in response thereto select and monitor at least one predetermined sensor adjacent to a triggered sensor, and at least one recording component configured to record acoustical responses from at least one of the at least two acoustic sensors, the at least one recording component being responsive to the multiplexing circuit;

forming a connection between the acoustic monitoring device and the solid medium capable of detecting damage of the solid medium; and monitoring the sensors for a triggering event.

12. The method of claim 11, further comprising the step of identifying the source of the damage.

13. The method of claim 11, further comprising the step of assessing the magnitude of the damage.

14. The method of claim 11, further comprising the step of recording acoustic emissions from at least one adjacent sensor to a monitored sensor registering a triggering event.

15. The method of claim 14, further comprising the step of recording acoustic emissions from at least two adjacent sensors to a monitored sensor registering a triggering event.

16. The method of claim 11, wherein the triggering event comprises an acoustic signal of a predetermined amplitude.

17. The method of claim 11, further comprising the step of locating an acoustic source with at least three sensors connected to a linear solid medium.

18. The method of claim 11, further comprising the step of locating an acoustic source with at least four sensors connected to a planar solid medium.

19. The method of claim 11, further comprising the step of locating an acoustic source with at least five sensors connected to a spatial solid medium.

20. The method of claim 11 further comprising the steps of:

sensing a triggering event; and responding to the sensed triggering event by utilizing the multiplexing circuit to identify which of the at least two acoustic sensors was triggered and select and monitor at least one sensor adjacent to the triggered sensor.

21. An acoustic monitoring device, comprising the components of:

at least two acoustic sensors capable of sensing acoustic vibrations from a solid medium;

a triggering mechanism responsive to a set parameter first occurring at one of the acoustic sensors;

a multiplexing circuit connected to be triggering mechanism and configured to receive a triggering event and in response thereto select and monitor one of:

at least two predetermined sensors adjacent to a triggered sensor, and a triggered sensor and at least one predetermined sensor adjacent to the triggered sensor; and at least one recording component configured to record signals from the monitored acoustic sensors.

22. The acoustic monitoring device according to claim 21, wherein the multiplexing circuit comprises means to communicate to the at least one recording component which of the at least two acoustic sensors are being monitored.

23. An acoustic monitoring device, comprising the components of:

at least two acoustic sensors capable of sensing acoustic vibrations from a solid medium;

a triggering mechanism responsive to a set parameter first occurring at one of the acoustic sensors;

a multiplexing circuit connected to the triggering mechanism and configured to receive a triggering event and in response thereto simultaneously monitor one of:

at least two sensors adjacent to a triggered sensor, and a triggered sensor and at least one sensor adjacent to the triggered sensor; and at least one recording component configured to record signals from the simultaneously monitored sensors.

* * * * *